United States Patent [19]

Cocozza

[11] Patent Number: 5,250,287

[45] Date of Patent: Oct. 5, 1993

[54] MULTI-DOSE INSUFFLATOR FOR MEDICAMENTS IN POWDER FORM

[75] Inventor: Salvatore Cocozza, Milan, Italy

[73] Assignee: Miat S.p.A., Milan, Italy

[21] Appl. No.: 881,433

[22] Filed: May 11, 1992

[30] Foreign Application Priority Data

Jun. 14, 1991 [IT] Italy .................. MI91 A 001643

[51] Int. Cl.$^5$ .................................... A61L 9/04
[52] U.S. Cl. ............................ 424/45; 514/255; 128/203.21
[58] Field of Search .............. 424/45; 514/255; 128/203.21

[56] References Cited

U.S. PATENT DOCUMENTS

| | | | |
|---|---|---|---|
| 2,992,645 | 7/1961 | Fowler | 424/45 |
| 3,895,111 | 7/1975 | Corey | 514/255 |
| 4,884,565 | 12/1989 | Cocozza | 128/203.21 |
| 5,033,463 | 7/1991 | Cocozza | 128/203.21 |

FOREIGN PATENT DOCUMENTS 0424790 8/1991 European Pat. Off. .

Primary Examiner—Thurman K. Page
Assistant Examiner—W. Benston
Attorney, Agent, or Firm—Ladas & Parry

[57] ABSTRACT

A multi-dose insufflator for the nasal administration of medicaments in fine or micronized powder form comprises a reservoir unit (34), a unit (60, 64) for withdrawing and metering the medicament contained in the reservoir unit, and an insufflation unit (42, 26) comprising a manually operated pump (42) for generating an air stream within a channel (26) for conveying an individual dose of medicament into the nasal cavity of the patient. The withdrawal and metering unit comprises a conveyor device (60) provided with at least one cup (64) for withdrawing a dose of medicament from the reservoir (34) and conveying it into an insufflation position. The cup (64) has a coaxial base hole (66) through which the air stream generated by the pump passes when the cup is in the insufflation position. The hole (66) has a size substantially smaller than the mouth of the cup (64) and such as to prevent the powder medicament falling through the hole, by virtue of the "arching" effect.

22 Claims, 3 Drawing Sheets

MULTI-DOSE INSUFFLATOR FOR MEDICAMENTS IN POWDER FORM

This invention relates to insufflators for the nasal administration of medicaments in fine or micronized powder form. In known insufflators, the powder to be administered is usually contained in suitable rigid gelatin capsules. These insufflators comprise a device for piercing the capsule, through which an air stream is passed to remove the powder from the capsule and serve as a vehicle for administering the powder. The air stream is produced by a suitable manually operated pump.

Various types of insufflator are known. In these, the capsule containing the medicament in the form of a fine or micronized powder, which usually occupies about ⅓ of the inner volume of the capsule, is placed in an appropriate seat provided in the apparatus and is then pierced or opened so that the air stream which is made to pass through the seat entrains the powder medicament.

Said piercing device comprises one or more needles or points, usually two coaxially opposed points arranged to form two corresponding opposing apertures such that the air stream which passes through these opposing apertures can entrain the powder contained in the capsule. In this respect reference should be made to U.S. Pat. No. 3,906,950 in which the points are arranged vertically. However, besides being considerably complicated this insufflator has the further drawback that when the capsule is pierced by the two opposing vertically arranged points of the piercing device, the combined effect of the force of gravity acting on the powder contained in the capsule and the dragging action on the powder exerted by the lower point as it withdraws from the capsule results in an appreciable quantity of powder falling outside of the capsule.

The action of the air stream, which in this specific case is produced by a lower hand pump, is unable to completely expel the quantity of powder which has fallen from the capsule, with the result that some powder medicament is wasted. In addition in the long term, powder accumulates especially in the pump, requiring periodical cleaning of the insufflator.

A similar insufflator, but of much simpler structure, is produced by the British firm FISONS LIMITED and known by the brand name of RINOFLATOR. In this there is only one piercing point, which is vertical, faces upwards and is coaxial with the capsule and the passage channel for the air stream. The length of the point is such that it passes completely through the capsule axially. However, this insufflator has the same, if not more serious, drawbacks as the preceding case with regard to the escape of powder from the lower hole of the capsule and the accumulation of powder within the apparatus. This is confirmed by the fact that this insufflator is sold together with a brush for removing the powder which accumulates within it.

A further known apparatus is that described in U.S. Pat. No. 4,013,075, which is available either as an inhaler or an insufflator. In it the capsule is again arranged vertically, parallel to the exit channel for the air stream.

The capsule is opened by cutting the two end caps of the capsule. This apparatus is however of complicated and costly manufacture, as it is composed of rather elaborate parts, including two metal blades of special shape. In addition, on cutting the two end caps of the capsule there is again an appreciable wastage of powder. An insufflator which overcomes the drawbacks of the aforesaid insufflators is that described in U.S. Pat. No. 4,884,565, having the same inventor and the proprietor as the present patent application. In addition to the conventional hand pump, the insufflator comprises a body having an air entry aperture in communication with the pump interior, this aperture being coaxial with a substantially vertical exit channel for conveying the entering air mixed with the powder medicament contained in a capsule. A device is provided comprising opposing points movable horizontally in both directions to pierce the capsule. This latter is arranged in a suitable seat comprising two opposing axial holes. The seat is formed in an element which is rotatable relative to said body to assume at least two different positions, namely a first position or capsule piercing position, in which the capsule can be pierced axially by said points, which can pass through said coaxial holes in the seat, and a second position or delivery position, which is substantially rotated through 90° from the first position and in which one of the seat holes is coaxial with the air exit channel whereas the other hole communicates with the air entry aperture.

As is well known, the capsules normally used in insufflators and inhalers are of overall cylindrical shape, with their two ends in the form of a spherical cap. Known capsules are normally formed from two parts, one inserted into the other. They are generally formed of substantially rigid gelatin.

In addition to those of the already stated patent documents, other dispensing devices which use said capsules are described for example in U.S. Pat. Nos. 3,807,400 and 3,991,761.

In these known dispensing devices the holes can be made in various regions of the capsule, but preferably at its two opposite ends or in proximity thereto. The holes are formed by various suitable means.

It has been found experimentally that when the capsule has been opened, complete expulsion of its powder depends not only on the piercing means but, in particular, on the physical characteristics of the capsule.

In this respect, the wear suffered by known capsule opening means, the variability in the physical characteristics of the gelatin capsule, and the formation of fragments of the capsule casing, can result in incomplete emptying of the open capsule and/or operational defects in the dispensing device, with repercussions on its efficiency.

As is well known to the expert of the art, the capsule gelatin generally have a water content of 8%–15%. It is difficult to obtain and maintain a homogeneous water content within 10%–11%, which has proved to be the optimum range.

In this respect, if the capsule gelatin has a water content below this range, the piercing or opening means can fracture the capsule or produce extensive cracks therein, to the extent of compromising the operation of the device used.

If instead the capsule has a water content above this range, the piercing means may be ineffective, or produce inwardly bent edges at the opening due to the inward deformation of the capsule gelatin. These inwardly extending edges can retain significant quantities of medicament within the capsule.

From the aforestated it is apparent that the key element on which the proper operation of an administration device (whether inhaler or insufflator) depends is first and foremost the capsule. However, as indicated, the characteristics of gelatin capsules are variable. At the moment of use, these characteristics may differ from the optimum, resulting in the stated difficulties.

To overcome the problems deriving from capsules, inhalers have been developed known as "multi-dose" because they are provided with a reservoir containing a quantity of medicament in powder form sufficient for several doses. Such multi-dose inhalers have undoubted advantages in terms of comfort and marketability. An inhaler of this type is described in EP-A-0,069,715, and in addition to the reservoir for the powder medicament comprises a device for withdrawing and metering the medicament from the reservoir. This withdrawing and metering device comprises a baffle of a certain thickness and containing a certain number of through holes. The baffle can be moved from a position in which a part of said holes is filled by mechanical means with powder medicament taken from the reservoir, and another position in which the holes filled with medicament are located within a channel. When the user sucks through a suction mouthpiece connected to the channel, air flows into this latter to remove the powder medicament from said holes.

A scraper device is also provided to scrape the powder within the baffle holes to the correct level on the side facing the reservoir. According to the inventor this scraper should ensure complete filling of said holes, hence providing constant doses. Although this scraper is stated in said document to be optional, it must be considered as essential for the proper operation of the inhaler, because in its absence an extremely variable dose is obtained. In this respect, it is very easy for the respective holes not be completely filled with powder medicament because of the poor flowability of the powders used.

However, even with the scraper present the baffle holes are not always completely filled, so that there is still an excessive dosage variability which, especially in the case of medicaments to be dispensed in very small doses, could cause a substantial variability in the activity of the medicament.

A multi-dose inhaler which overcomes the drawbacks of this latter inhaler is described in U.S. Pat. No. 5,033,463 having the same inventor and proprietor as the present application. This inhaler comprises a reservoir for the medicament in powder form, and a metering device which is provided with a conveyor having at least one cup of predetermined dimensions, each cup of the conveyor comprising two coaxial holes of equal dimensions, into which a slider or piston can precisely enter and move in both directions to cause the dose of medicament contained in the cup to fall into a chamber in which the medicament is mixed with air, this chamber being connected to a mouthpiece.

In contrast to inhalers, in the case of insufflators it has not yet been possible to construct a multi-dose insufflator. The main object of the present invention is to provide a multi-dose insufflator, i.e. having a reservoir containing a quantity of medicament in powder form sufficient for several doses.

A further object of the invention is to provide a multi-dose insufflator of simple and low-cost construction, taking account of the fact that it is able to dispense a considerable number of doses.

A further object is to provide a multi-dose insufflator which can be recharged when the powder medicament contained in the reservoir has been completely consumed.

The said main object is attained according to the present invention by a multi-dose insufflator comprising a reservoir unit for the medicament in powder form, a unit for withdrawing and metering the medicament contained in the reservoir unit, and an insufflation unit comprising a manually operated pump for generating an air stream within a channel for conveying an individual dose of medicament into the nasal cavity of the patient; the withdrawal and metering unit comprising a conveyor device provided with at least one cup for withdrawing a dose of powder medicament from the reservoir and conveying it into an insufflation position; the cup having a base hole coaxial with the cup itself, and through which the air stream generated by the pump passes when the cup is in the insufflation position; the base hole in the cup having a size substantially smaller than that of the cup mouth and such as to prevent the powder medicament falling through said base hole, by virtue of the "arching" effect. An insufflator is hence obtained having all the advantages of multi-dose dispensers, because capsules are not used. The multi-dose insufflator of the invention is formed from a small number of units which, as will be seen from the embodiment described hereinafter, can be constructed in a very simple and low-cost manner.

Conveniently the conveyor device is in the form of a disc rotatable about its own axis.

In one embodiment of the present invention the insufflator is composed of two parts rotatable one relative to the other about the axis of the conveyor disc, one of these parts comprising the conveyor disc and pump, and the other comprising the reservoir and the insufflation channel.

According to a further embodiment of the invention the multi-dose insufflator is provided with means for producing vibrations. The effect obtained facilitates the running of the powder from the reservoir unit to the relative conveyor cup and its complete filling.

The means for generating vibrations are preferably operated directly by the movement of the conveyor device. The multi-dose insufflator is conveniently provided with a conventional device for indicating when the reservoir is empty of powder medicament. The insufflator can be of the disposable type so that when the powder medicament contained in the reservoir has been consumed it is thrown away.

According to a further embodiment of the present invention the insufflator can be recharged, for example using sachets of medicament, recharging taking place through a suitable cover or window provided on the reservoir, or a reservoir unit of removable type can be provided for this purpose, which when empty can be replaced with a new reservoir unit full of powder medicament. The invention will be more apparent from the description of one embodiment thereof given hereinafter by way of non-limiting example. In this description reference is made to the accompanying drawings.

Figure 1:
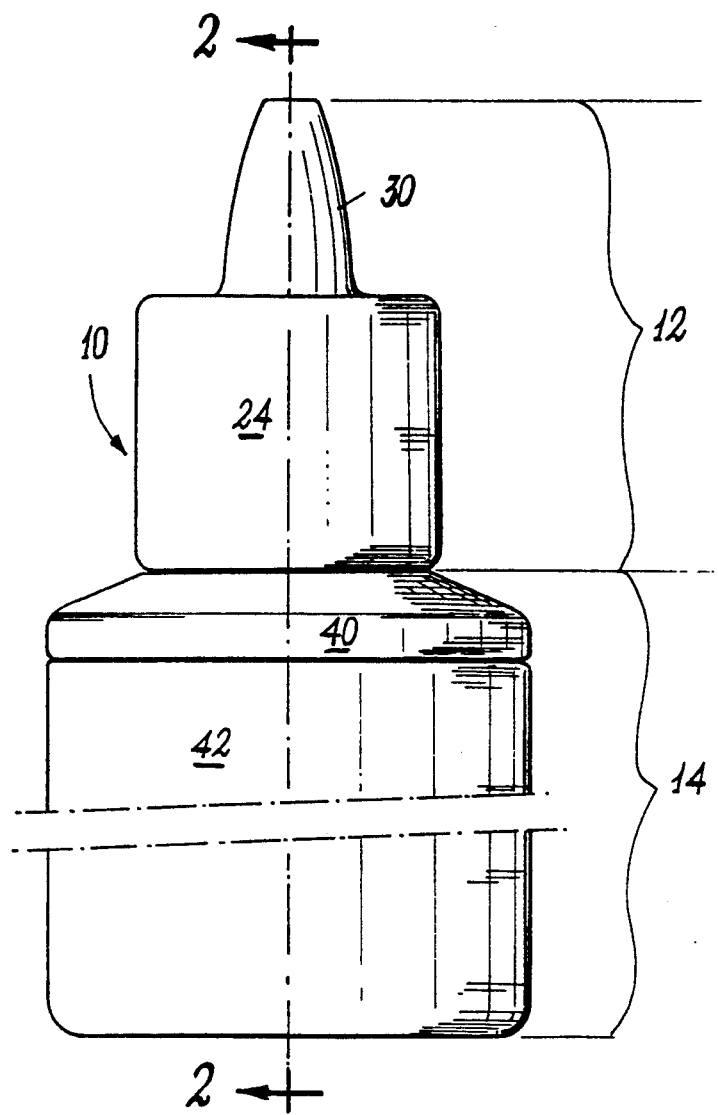
FIG. 1 is a side view of the multi-dose insufflator.
Figure 2:
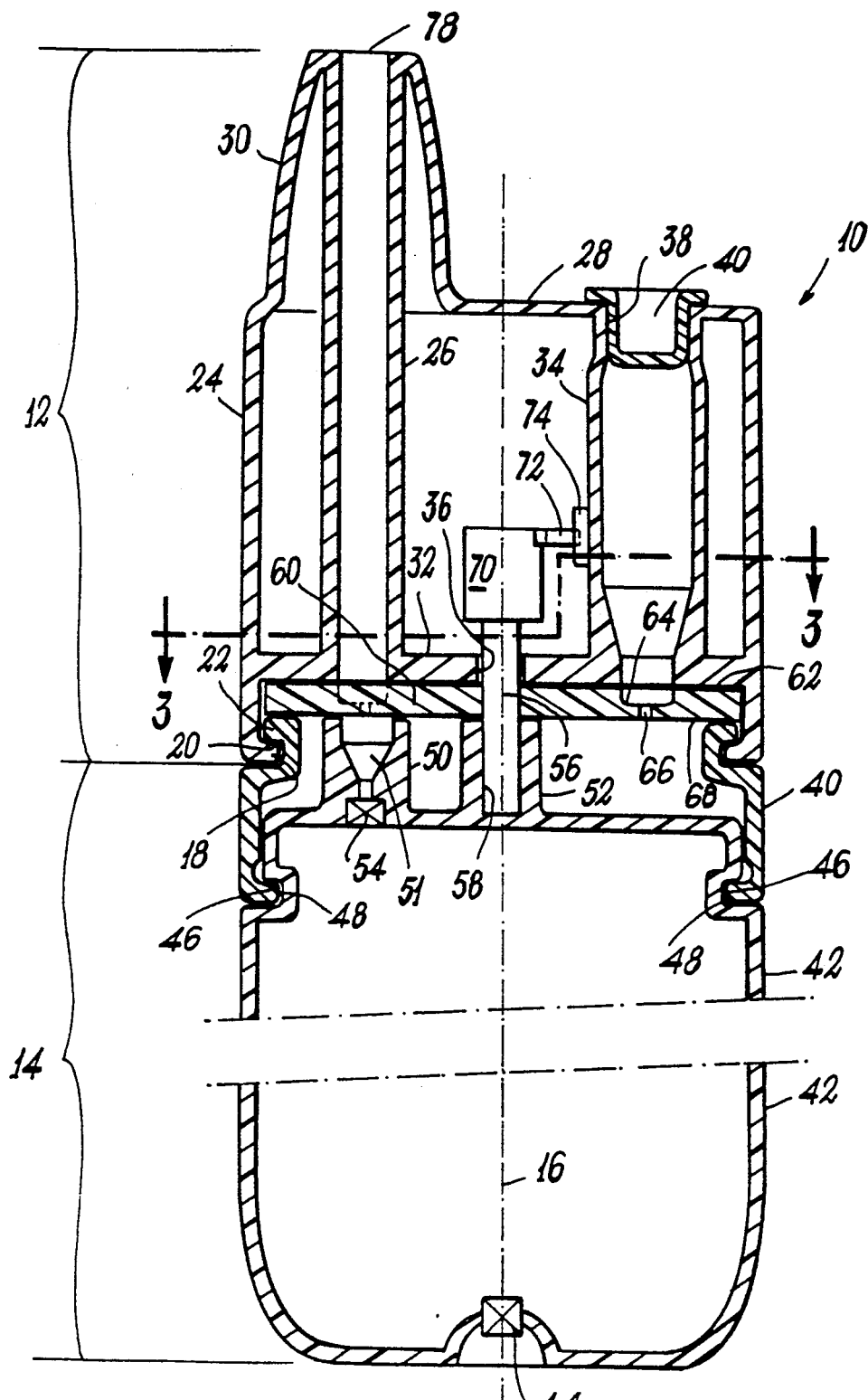
FIG. 2 is an enlarged vertical cross-section taken on the line 2—2 of FIG. 1.
Figure 3:
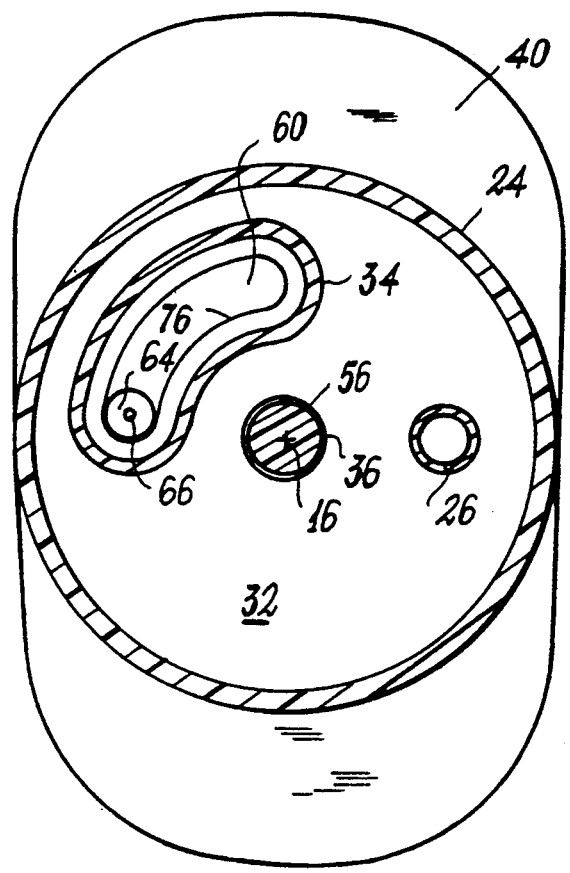
FIG. 3 is a horizontal cross-section on the line 3—3 of FIG. 2.

The multi-dose insufflator 10 shown in the figures consists substantially of two parts 12 and 14 (FIGS. 1 and 2) connected together in such a manner that one can rotate relative to the other about a vertical axis 16 (FIGS. 2 and 3).

The two parts can be snap-connected by forcing one part (12) onto the other (14) such that the circular lip 18 of the upper part 12 snap-enters the circular groove 20 of the lower part 14, passing beyond the lip 22 of said lower part. The groove 20 hence also acts as a guide for the mutual rotation of the two parts 12 and 14.

The upper part 12 of the insufflator 10 consists of a substantially cylindrical outer casing 24, and a vertical tube 26 rigid with the outer casing 24. The upper end portion of the tube 26 projects from the circular upper wall 28 of the cylindrical casing 24, its upper end being connected to the upper wall 28 in such a manner as to form an adaptor 30 for insertion into the nostril of the patient. A circular baffle 32 is provided rigid with the outer casing 24 of the upper part 12, in a manner parallel to the upper wall 28 of the casing 24. The lower end of the tube 26 is fixed onto the baffle 32. The lower end of the reservoir 34 for the medicament in powder form is also fixed to the baffle 32, the upper end of said reservoir being fixed to the upper wall 28 of the cylindrical casing 24. The baffle 32 has a circular central hole 36 the purpose of which is explained hereinafter.

The reservoir 34 has an upper opening 38 closed by a stopper 40 to enable the reservoir 34 to be recharged with a quantity of medicament in powder form, for example supplied in sachets containing medicament for a predetermined number of doses. If the insufflator is of the disposable type the stopper 40 of the reservoir 34 can be of the type not removable by the patient once it has been position, so that the reservoir 34 cannot be recharged.

The lower part 14 of the insufflator 10 consists of a connection element 41 between the upper part 12 and a hand pump comprising a hollow body of "soap" shape formed of atoxic elastic material and easily deformable by squeezing gently with the fingers so as to reduce its internal volume. The pump 42 is provided conventionally with an air intake in its lower face, closed by a non-return valve 44 which enables air to enter following the production of vacuum within the pump, but prevents air leaving when the pump is squeezed.

The pump also comprises a number of horizontal recesses, of which two can be seen in FIG. 2 (indicated by 46, in cross-section), to receive corresponding lip-shaped portions 48 projecting inwards from the lower edge of the connection element 41, to fix this latter to the pump 42. The pump also comprises two cylindrical projections 50 and 52, the first of which lowerly houses a second non-return valve 54 communicating upperly with a funnel-shaped vertical channel 51. The greater-diameter end of the funnel faces upwards. The other cylindrical protuberance 52 comprises an upperly open coaxial cylindrical cavity 58 for receiving the lower end of a vertical shaft 56 which is forced into the cavity 58. A horizontal disc 60 is fixed onto the shaft 56 to rotate rigidly therewith.

The disc 60 comprises in its upper face 62 a cup-shaped recess 64 the base of which comprises a coaxial through hole 66 which opens into the lower face 68 of the disc 60.

The hole 66 has a much smaller diameter than the cup 64. This diameter is established on the basis of the size of the particles of the powder medicament such that this latter cannot fall, other than in an absolutely negligible quantity, out of the cup 64 hole 66 because of the "arching effect" or rather "dome" which arises between the medicament particles when the cup 64 is filled with it, and also because of the cohesion between the particles, which is greater the smaller they are. The result is that once the cup has been filled with the medicament in powder form, the powder falling from the reservoir 34 into the cup 64 by gravity and possibly because of vibration produced by suitable means, the medicament remains in the cup and cannot escape from it through the hole 66.

The cup 64 has conveniently the shape of a normal cup. However it can also be of other shapes such as conical, frusto-conical or cylindrical.

The shaft 56 which, as stated, is rigid with the pump 42 and disc 60, carries fixed on its upper end a cap 70 provided with a horizontal toothed sector 72 centered on the axis of the shaft 56 to produce vibrations in cooperation with a vertical rib 74 rigid with the reservoir 34, following rotation of the shaft 56. As can be seen from FIG. 3, the reservoir 34, seen in plan view, is of "bean" shape. At the lower end of the reservoir 34 there is an exit aperture 76 for the powder medicament, also of bean shape. The operation of the multi-dose insufflator 10 will now be briefly described. With reference to FIG. 3 it will be assumed that the cup 64 of the conveyor disc 60 is in the angular position shown in this figure, and which will be known as the starting position. If the upper part 12 of the insufflator 10 is now rotated clockwise about its lower part by means of the hands, the cup 64 travels along the entire length of the aperture 76 of the reservoir 34, so being filled with the medicament in powder form contained in the reservoir. The said toothed sector 72, which rotates with the shaft 56 and the conveyor disc and which interferes with the rib 74 fixed to the reservoir 34, produces vibrations at least while the cup 64 lies under the aperture 76, so ensuring that the powder will flow and completely fill the cup. Continuing to mutually rotate the two parts 12 and 14 of the insufflator 10, at a certain moment the cup 64 reaches a position corresponding with the lower end of the tube 26 and with the exit valve 54 for the air from the pump. This angular position of the cup 64 (shown by dashed lines in FIG. 2) will be known as the insufflation position. It is now merely necessary for the patient to place the adaptor 30 in a nostril and then squeeze the pump 42 with the fingers in conventional manner, to cause an air stream, leaving the valve 54, to pass through the hole 66 in the cup 64 and remove the entire dose of medicament contained therein, to then rise into the tube 26 and leave through its upper opening 78, and into the nasal cavity of the patient.

As is apparent, the multi-dose insufflator 10 is very easy to use, besides being of simple structure and manufacture. The two angular positions, i.e. the starting position (FIG. 3) and the insufflation position (cup 64 at the tube 26) can be defined by respective marks or notches on the two mutually rotatable parts 12 and 14 of the insufflator 10, or in other conventional ways for their identification.

The insufflator can be provided with a conventional device for counting the doses dispensed based on the rotation of the conveyor disc, and hence indicate when the medicament contained in the reservoir has been totally consumed.

Because of the removable stopper 40 which closes the upper opening 38 of the reservoir 34, this latter can be easily refilled with a new supply of medicament, which can be supplied to the patient for example in sachets.

The non-return valve 54 shown in FIG. 2 is not indispensable in view of the negligible quantity of powder medicament which could fall through the hole 66 in the cup 64. Because of this valve, even this small quantity of powder which falls onto the valve, normally closed except for the short insufflation period, is recovered and insufflated.

It will be apparent to the expert of the art that the multi-dose insufflator could have as its only rotary part the conveyor disc 60, in this case no longer rigid with the pump 42 or connection element 10, these latter then being fixed with respect to the upper part 12 of the insufflator. In this case the conveyor disc 60 must be provided with independent means to rotate it about its axis of rotation.

This can be achieved by releasing the shaft 56 from the pump 42 (i.e. eliminating the cylindrical protuberance 52) and prolonging the shaft upwards until it emerges from the upper wall 28 of the insufflator through a suitable aperture, the upper end of the shaft being provided with a knob or the like to manually rotate the conveyor disc.

Although the illustrated and described embodiment of the insufflator according to the invention is provided with a conveyor device of rotary disc type, it will be apparent to the expert of the art that it could be formed as a drawer movable in the two directions between a starting position corresponding to the reservoir exit (this exit being elongate in the direction of movement) and an insufflation position.

I claim:

1. A multi-dose insufflator (10) for the nasal administration of medicaments in powder form, comprising a reservoir unit (34) for the medicament in powder form, a unit (60, 64) for withdrawing and metering the medicament contained in the reservoir unit, and an insufflation unit (42, 26) comprising a manually operated pump (42) for generating an air stream within a channel (26) for conveying an individual dose of medicament into the nasal cavity of the patient; the withdrawal and metering unit (60, 64) comprising a conveyor device (60) provided with at least one cup (64) for withdrawing a dose of powder medicament from the reservoir and conveying it into an insufflation position; the cup having a base hole (66) coaxial with the cup itself, and through which the air stream generated by the pump (42) passes when the cup (64) is in the insufflation position; the base hole (66) in the cup (64) having a size substantially smaller than that of the mouth of the cup (64) and such as to prevent the powder medicament falling through said base hole (66), by virtue of the "arching" effect.

2. A multi-dose insufflator (10) as claimed in claim 1, wherein the conveyor device comprises a conveyor disc (60) rotatable about its axis (16).

3. A multi-dose insufflator as claimed in claim 2, wherein the insufflator (10) is composed of two parts (12, 14) rotatable one relative to the other about the axis (16) of the conveyor disc, one (14) of said parts comprising the conveyor disc and the pump (42), the other (12) comprising the reservoir (34) and the insufflation channel (26); the conveyor disc (60) having a single cup (64).

4. A multi-dose insufflator as claimed in claim 1, comprising means (72, 74) for producing vibrations to facilitate the fall of the powder medicament in the reservoir (34) and the filling of the relative cup (64).

5. A multi-dose insufflator as claimed in claim 1, comprising a device for indicating when the powder medicament in the reservoir (34) has been completely consumed.

6. A multi-dose insufflator as claimed in claim 1, wherein the reservoir (34) can be recharged with further medicament in powder form.

7. A multi-dose insufflator as claimed in claim 1, wherein the reservoir can be removed when empty and replaced with another reservoir full of medicament.

8. A multi-dose insufflator as claimed in claim 2, comprising means (72, 74) for producing vibrations to facilitate the fall of the powder medicament in the reservoir (34) and the filling of the relative cup (64).

9. A multi-dose insufflator as claimed in claim 3, comprising means (72, 74) for producing vibrations to facilitate the fall of the powder medicament in the reservoir (34) and the filling of the relative cup (64).

10. A multi-dose insufflator as claimed in claim 2, comprising a device for indicating when the powder medicament in the reservoir (34) has been completely consumed.

11. A multi-dose insufflator as claimed in claim 3, comprising a device for indicating when the powder medicament in the reservoir (34) has been completely consumed.

12. A multi-dose insufflator as claimed in claim 4, comprising a device for indicating when the powder medicament in the reservoir (34) has been completely consumed.

13. A multi-dose insufflator as claimed in claim 2, wherein the reservoir (34) can be recharged with further medicament in powder form.

14. A multi-dose insufflator as claimed in claim 3, wherein the reservoir (34) can be recharged with further medicament in powder form.

15. A multi-dose insufflator as claimed in claim 4, wherein the reservoir (34) can be recharged with further medicament in powder form.

16. A multi-dose insufflator as claimed in claim 5, wherein the reservoir (34) can be recharged with further medicament in powder form.

17. A multi-dose insufflator as claimed in claim 2, wherein the reservoir can be removed when empty and replaced with another reservoir full of medicament.

18. A multi-dose insufflator as claimed in claim 3, wherein the reservoir can be removed when empty and replaced with another reservoir full of medicament.

19. A multi-dose insufflator as claimed in claim 4, wherein the reservoir can be removed when empty and replaced with another reservoir full of medicament.

20. A multi-dose insufflator as claimed in claim 5, wherein the reservoir can be removed when empty and replaced with another reservoir full of medicament.

21. A multi-dose insufflator as claimed in claim 6, wherein the reservoir can be removed when empty and replaced with another reservoir full of medicament.

22. A multi-dose insufflator as claimed in claim 1 wherein the medicaments in powder form are fine or micronized form wherein 98% of the powder is between 4.5–80 micrometers.

* * * * *